US008669218B2

(12) United States Patent
Schiedel et al.

(10) Patent No.: US 8,669,218 B2
(45) Date of Patent: Mar. 11, 2014

(54) WC GEL

(71) Applicant: Henkel AG & Co. KGaA, Duesseldorf (DE)

(72) Inventors: Marc-Steffen Schiedel, Monheim (DE); Brigitte Giesen, Duesseldorf (DE); Petra Plantikow, Duesseldorf (DE); Luca Bellomi, Duesseldorf (DE); Karl-Heinz Scheffler, Duesseldorf (DE)

(73) Assignee: Henkel AG & Co. KGaA, Duesseldorf (DE)

( * ) Notice: Subject to any disclaimer, the term of this patent is extended or adjusted under 35 U.S.C. 154(b) by 0 days.

(21) Appl. No.: 13/975,057

(22) Filed: Aug. 23, 2013

(65) Prior Publication Data

US 2014/0005092 A1 Jan. 2, 2014

Related U.S. Application Data

(63) Continuation of application No. PCT/EP2012/052446, filed on Feb. 14, 2012.

(30) Foreign Application Priority Data

Feb. 25, 2011 (DE) .......................... 10 2011 004 771

(51) Int. Cl.
C11D 1/88 (2006.01)
C11D 3/22 (2006.01)
C11D 3/50 (2006.01)

(52) U.S. Cl.
USPC ........... 510/191; 510/101; 510/192; 510/238; 510/403; 510/470; 510/475; 510/490

(58) Field of Classification Search
USPC ......... 510/101, 191, 192, 238, 403, 470, 475, 510/490
See application file for complete search history.

(56) References Cited

U.S. PATENT DOCUMENTS

| 6,667,286 B1 | 12/2003 | Dettinger et al. |
| 2004/0211316 A1 | 10/2004 | Collins |
| 2007/0178056 A1 | 8/2007 | Mock-Knoblauch et al. |
| 2012/0178824 A1* | 7/2012 | Konig et al. ............... 514/772.1 |

FOREIGN PATENT DOCUMENTS

| DE | 102010028352 A1 | 11/2011 |
| EP | 1318191 A1 | 6/2003 |
| WO | 2012/095404 A1 | 7/2012 |

OTHER PUBLICATIONS

PCT International Search Report (PCT/EP2012/052446) dated Apr. 16, 2012.
Al-Sabagh et al., "Water-based non-ionic polymeric surfactants as oil spill dispersants", Journal of Chemical Technology and Biotechnology, vol. 74, pp. 1075-1081, 1999.

* cited by examiner

Primary Examiner — Brian P Mruk
(74) Attorney, Agent, or Firm — Krista Kostiew

(57) ABSTRACT

An adherent gelled or pasty composition for cleaning and/or scenting a toilet, wherein the composition is applied internally onto the toilet ceramic and is rinsed off only after several flushing operations, the composition comprising: a surfactant selected from the group consisting of alkylpolyglycosides, amphoacetates, amphodiacetates, betaines, fatty alcohol ethercarboxylic acids, fatty acid sarcosinates, cocamidopropylamine oxide, aminopropionates, and biosurfactants; perfume; and water; wherein the composition comprises, as an adhesion promoter, an ester of polyisobutene succinic acid, and wherein the composition is free of further adhesion promoters and surfactants.

13 Claims, No Drawings

WC GEL

FIELD OF THE INVENTION

The present invention generally relates to an adherent gelled or pasty composition for cleaning and/or scenting a toilet. This composition is applied internally onto the toilet ceramic and is rinsed off only after several flushing operations.

BACKGROUND OF THE INVENTION

Scented toilet cleansers have already been used for some time to clean, disinfect, and scent toilets. In their original form they are used as solid blocks under the rim of the bowl ("rim blocks") and in the water tank ("in-tank blocks" or "cistern blocks"). In recent years, aesthetics and performance have acquired ever-increasing significance. This has resulted, for example, in the development of gelled or liquid scented cleansers that are offered in part in multi-chamber containers and thus allow the combination of a cleaning agent, which is delivered upon activation of the toilet flushing system, with constant room scenting.

Conventional solid, liquid, or even gelled scented cleansers are introduced into the flush toilet by means of corresponding apparatuses, called "toilet baskets." These toilet baskets are rejected by some consumers, however, for hygienic reasons. On the one hand, germs can become established in the course of the service life, which can result in formation of an unattractive biofilm. On the other hand, refilling or replacement of the basket is perceived as unhygienic or even repellent because of the contact that is required, even if there is no visible biofilm adhering to the apparatus. Lastly, certain consumers perceive it as a disadvantage that the basket can be shifted by a toilet brush when the toilet is cleaned.

Self-adherent agents, which are applied directly onto the toilet ceramic and are gradually rinsed off, have therefore been developed. EP 1086199 B1, for example, describes a solid or pasty adherent sanitary agent that encompasses water, anionic and/or nonionic and/or amphoteric surfactants, scents, an adhesion promoter, and optionally further usual constituents, where the adhesion promoter is to be selected from the group consisting of polyalkoxyalkanes, celluloses, starch, alginates, diurethanes, gelatin, pectins, oleylamines, alkyldimethylamine oxides, stearates, sodium dodecylbenzenesulfonate, agar-agar, gum Arabic, locust bean flour, polyacrylate, polyvinyl alcohol, and polyvinylpyrrolidone. Similar pastes are also described in EP 1318191 B1, although in this the adhesion promoter is to be selected from the group of the block copolymers encompassing oligo- or polyethylene oxide and/or oligo- and/or polypropylene oxide and/or oligo- and/or polybutylene oxide.

It has now been found that an adherent gelled or pasty composition that contains at least one surfactant from the group consisting of alkylpolyglycosides, amphoacetates, amphodiacetates, betaines, fatty alcohol ethercarboxylic acids, fatty acid sarcosinates, cocamidopropylamine oxide, aminopropionates, and biosurfactants, perfume, and water, as well as an ester of polyisobutene succinic acid as the only adhesion promoter, can be formulated. This product has a clear and transparent aesthetic and possesses, after application, good dimensional stability over the entire rinsing cycle. Even if the composition does not have water flowing over it for a period of a few hours because the toilet flushing system is not actuated, its shape does not change nor does it become unsightly.

The subject matter of the invention is therefore an adherent gelled or pasty composition for cleaning and/or scenting a toilet, which composition is applied internally onto the toilet ceramic and is rinsed off only after several flushing operations, containing at least one surfactant from the group consisting of alkylpolyglycosides, amphoacetates, amphodiacetates, betaines, fatty alcohol ethercarboxylic acids, fatty acid sarcosinates, cocamidopropylamine oxide, aminopropionates, and biosurfactants, perfume, water, and as adhesion promoter an ester of polyisobutene succinic acid, which is free of further adhesion promoters and surfactants.

This gelled or pasty composition is advantageously applied with an applicator. In an embodiment, two gelled or pasty formulations are introduced into a two-chamber applicator that is also described in patent application DE 10 2012 028352.5.

Furthermore, other desirable features and characteristics of the present invention will become apparent from the subsequent detailed description of the invention and the appended claims, taken in conjunction with the accompanying drawings and this background of the invention.

BRIEF SUMMARY OF THE INVENTION

In an embodiment, an adherent gelled or pasty composition for cleaning and/or scenting a toilet, wherein the composition is applied internally onto the toilet ceramic and is rinsed off only after several flushing operations, the composition comprises: a surfactant selected from the group consisting of alkylpolyglycosides, amphoacetates, amphodiacetates, betaines, fatty alcohol ethercarboxylic acids, fatty acid sarcosinates, cocamidopropylamine oxide, aminopropionates, and biosurfactants; perfume; and water; wherein the composition comprises, as an adhesion promoter, an ester of polyisobutene succinic acid, and wherein the composition is free of further adhesion promoters and surfactants.

DETAILED DESCRIPTION OF THE INVENTION

The following detailed description of the invention is merely exemplary in nature and is not intended to limit the invention or the application and uses of the invention. Furthermore, there is no intention to be bound by any theory presented in the preceding background of the invention or the following detailed description of the invention.

Substances that also serve as ingredients of cosmetic agents are designated below, as applicable, in accordance with the International Nomenclature of Cosmetic Ingredients (INCI). Chemical compounds carry an INCI name in English; plant-based ingredients are listed exclusively according to Linnaeus in Latin; so-called "trivial" names such as "water," "honey," or "sea salt" are likewise indicated in Latin. The INCI names may be gathered from the International Cosmetic Ingredient Dictionary and Handbook—Seventh Edition (1997), which is published by The Cosmetic, Toiletry, and Fragrance Association (CTFA), 1101 17th Street NW, Suite 300, Washington D.C. 20036, USA, and contains more than 9,000 INCI names as well as references to more than 37,000 trade names and technical designations, including the relevant distributors from more than 31 countries. The International Cosmetic Ingredient Dictionary and Handbook assigns the ingredients to one or more chemical classes, for example "polymeric ethers," and one or more functions, for example "surfactants—cleansing agents," which it in turn explains further, and to which reference may likewise be made hereinafter.

The indication "CAS" means that the series of numbers that follows is a Chemical Abstracts Service designation.

In the context of the present invention, fatty acids or fatty alcohols or derivatives thereof represent, unless otherwise indicated, branched or unbranched carboxylic acids or alcohols or derivatives thereof having by preference 6 to 22 carbon atoms, in particular 8 to 20 carbon atoms, particularly preferably 10 to 18 carbon atoms, extremely preferably 12 to 16 carbon atoms, for example 12 to 14 carbon atoms. The first-named are preferred in particular for environmental reasons because their plant derivation means they are based on renewable raw materials, but without limiting the teaching of the present invention to them. In particular, the oxo alcohols obtainable, for example, from Roelen oxosynthesis, or derivatives thereof, having by preference 7 to 19 carbon atoms, in particular 9 to 19 carbon atoms, particularly preferably 9 to 17 carbon atoms, extremely preferably 11 to 15 carbon atoms, for example 9 to 11, 12 to 15, or 13 to 15 carbon atoms, are correspondingly usable.

An ester of polyisobutene succinic acid as described in patent application EP 11150613.5 is used as an adhesion promoter in the composition according to the present invention. "Polyisobutene succinic acid" is understood as oligomeric or polymeric macromolecules having an oligomer residue or polymer residue that is derived from isobutene and that comprises at one of its termini one or two residues derived from succinic acid, i.e., residues of formula BS

(BS)

and correspondingly 2 or 4 carboxyl groups, as well as mixtures thereof.

Polyisobutene succinic acids can therefore be described by the following formulas IIa and IIb):

(IIa)

(IIb)

where PIB in formula IIa denotes a monovalent oligomer residue or polymer residue derived from polyisobutene, and PIB' in formula IIb denotes a divalent oligomer residue or polymer residue derived from polyisobutene.

In the esters of polyisobutene succinic acid that are used according to the present invention, at least one of the carboxyl groups is present in the form of the ester with a poly-$C_2$ to $C_4$ alkylene glycol or a poly-$C_2$ to $C_4$ alkylene glycol mono-$C_1$ to $C_{22}$ alkyl ether. Such esters can be described by the general formulas Ia and Ib:

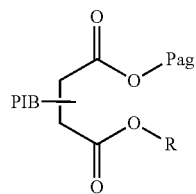

(Ia)

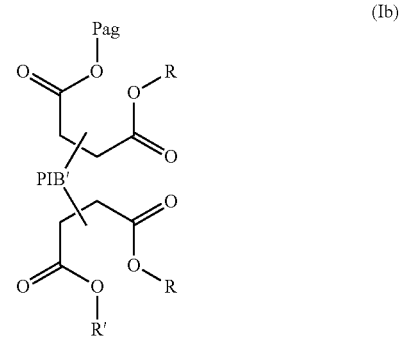

(Ib)

in which PIB and PIB' have the meanings indicated previously for formulas IIa and IIb, R and R' mutually independently denote water or Pag, and Pag denotes a residue derived from a poly-$C_2$ to $C_4$ alkylene glycol or from a poly-$C_2$ to $C_4$ alkylene glycol mono-$C_1$ to $C_{22}$ alkyl ether. In formulas Ia and Ib, R denotes in particular hydrogen.

"Poly-$C_2$ to $C_4$ alkylene glycols" are understood as linear or branched oligomers or polymers that are constructed substantially from repeating units of the formula -A-O— (hereinafter also called "alkylene oxide repeating units") in which A denotes $C_2$ to $C_4$ alkanediyl, and that have hydroxyl groups at their termini.

"Poly-$C_2$ to $C_4$ alkylene glycol mono-$C_1$ to $C_{22}$ alkyl ethers" are understood as linear or branched oligomers or polymers that are constructed substantially from repeating units of the formula -A-O—, in which A denotes $C_2$ to $C_4$ alkanediyl, that have at one of their ends a $C_1$ to $C_{22}$ alkyl groups bound via oxygen and have hydroxyl groups at the other terminus or other termini.

In these poly-$C_2$ to $C_4$ alkylene glycols or poly-$C_2$ to $C_4$ alkylene glycol mono-$C_1$ to $C_{22}$ alkyl ethers, the repeating units of the formula -A-O— can be the same or different. If the poly-$C_2$ to $C_4$ alkylene glycols or poly-$C_2$ to $C_4$ alkylene glycol mono-$C_1$ to $C_{22}$ alkyl ethers have different repeating units of the formula -A-O—, the latter can be arranged statistically, alternatingly, or in multiple, e.g. 2, 3, or 4 blocks. In a specific embodiment of the invention, the poly-$C_2$ to $C_4$ alkylene glycols or poly-$C_2$ to $C_4$ alkylene glycol mono-$C_1$ to $C_{22}$ alkyl ethers have different repeating units of the formula -A-O— that are arranged statistically.

"$C_2$ to $C_4$ alkanediyl" denotes in this connection a saturated divalent hydrocarbon residue having 2 to 4 carbon atoms, such as 1,2-ethanediyl, 1,2-propanediyl, 1,3-propanediyl, 1,4-butanediyl, 1,2-butanediyl, 1,3-butanediyl, 2,3-butanediyl, or 1-methyl-1,2-propanediyl.

"$C_1$ to $C_{22}$ alkyl" denotes in this connection a saturated acyclic monovalent hydrocarbon residue having 1 to 22 carbon atoms, in particular having 1 to 8 carbon atoms or 1 to 4 carbon atoms, such as methyl, ethyl, n-propyl, isopropyl, 1-butyl, 2-butyl, tert-butyl, isobutyl, n-pentyl, isopentyl, n-hexyl, isohexyl, n-heptyl, isoheptyl, n-octyl, isooctyl, 2-ethylhexyl, n-nonyl, isononyl, n-decyl, 2-propylheptyl, n-undecyl, n-dodecyl, n-tridecyl, myristyl, pentadecyl, palmityl (=cetyl), heptadecyl, octadecyl, nonadecyl, arachinyl, or behenyl.

"Polymer residues derived from isobutene," hereinafter also "polyisobutenyl residues," are understood as organic residues that are derived from linear or branched oligomers or polymers of isobutene and can contain polymerized into them up to 20 weight percent (wt %), by preference no more than 10 wt % $C_2$ to $C_{12}$ olefins other than isobutene, such as 1-butene, 2-butene, 2-methyl-1-butene, 2-methylpentene-1,2-methylhexene-1,2-ethylpentene-1,2-ethylhexene-1,2-propylheptene-1. Such residues can be described in the case of monovalent residues PIB by, for example, the following formulas

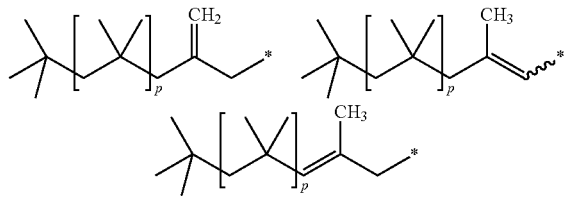

or in the case of divalent residues PIB' by, for example, the following formulas

in which the value p+2 corresponds to the degree of polymerization and indicates the number of isobutene units in the polyisobutene residue, and * signifies the linkage to the succinic acid (ester) residue. In these formulas some of the isobutene units, —$CH_2C(CH_3)_2$— for example, as a rule no more than 20 wt %, by preference no more than 10 wt %, can be replaced by $C_2$ to $C_{12}$ alkane-1,2-diyl groups different therefrom, derived from $C_2$ to $C_{12}$ olefins. The degree of polymerization p+2 is typically in the range from 5 to 100, in particular, in the range from 8 to 80, and especially in the range from 15 to 65.

In terms of the use according to the present invention in hydrogels, those esters of polyisobutene succinic acid that are made up, based on the total weight of the ester, of at least 50 wt %, in particular at least 70 wt % esters of formula Ia are preferred. The esters of polyisobutene succinic acid by preference contain, based on the total weight of the ester, less than 30 wt %, in particular less than 20 wt % esters of formula Ib.

In terms of the use according to the present invention in hydrogels, those esters of polyisobutene succinic acid whose polyisobutene residue of the ester has a number-average molecular weight in the range from 500 to 5000 Daltons, in particular in the range from 800 to 3600 Daltons, are preferred.

In a special embodiment of the invention, polyisobutene residues of the polyisobutene succinic acid esters have a narrow molecular weight distribution. The polydispersity is then equal by preference to at most 1.4, particularly preferably at most 1.3, in particular at most 1.2. "Polydispersity" is understood as the quotient of the weight-average molecular weight $M_w$ and number-average molecular weight $M_n$ ($PDI=M_w/M_n$).

In terms of the use according to present invention in hydrogels, those esters of polyisobutene succinic acid that are esterified with an alcohol selected from among poly-$C_2$ to $C_4$ alkylene glycols poly-$C_2$ to $C_4$ alkylene glycol mono-$C_1$ to $C_{22}$ alkyl ethers, or a mixture of said alcohols, are preferred, the alcohol or alcohols having a number-average molecular weight in the range from 500 to 15000 Daltons, in particular in the range from 800 to 10000 Daltons, and especially in the range from 1200 to 5000 Daltons.

It has furthermore proven advantageous if the alcohol that is esterified with the polyisobutene succinic acid is unbranched, i.e. is selected from among linear poly-$C_2$ to $C_4$ alkylene glycols and linear poly-$C_2$ to $C_4$ alkylene glycol mono-$C_1$ to $C_{20}$ alkyl ethers. Unbranched, i.e. linear poly-$C_2$ to $C_4$ alkylene glycols and linear poly-$C_2$ to $C_4$ alkylene glycol mono-$C_1$ to $C_{20}$ alkyl ethers can be described by formula (III) below:

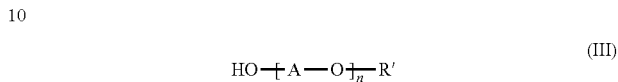

In this, A denotes $C_2$ to $C_4$ alkanediyl as defined above, which can be the same or different and is selected by preference from among 1,2-ethanediyl and 1,2-propanediyl. R' denotes hydrogen or $C_1$ to $C_{22}$ alkyl, in particular hydrogen or $C_1$ to $C_{10}$ alkyl, and especially hydrogen or $C_1$ to $C_4$ alkyl, e.g. methyl. The variable n indicates the average number of [A-O] repeating units (number average) and is typically in the range from 10 to 350, in particular in the range from 15 to 200.

Correspondingly, the residue Pag in formulas Ia and Ib by preference denotes a residue of the formula

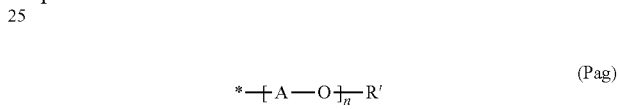

in which A, R, and n have the meanings indicated above, and * signifies the linkage to the oxygen atom of the polyisobutene succinic acid residue.

In formula III or in formula Pag, the repeating units of formula -A-O— can be the same or different. If formulas III or formulas Pag comprise different repeating units of formula -A-O—, the latter can be arranged statistically or in multiple, e.g. 2, 3, or 4 blocks. In a specific embodiment of the invention, formulas III or formulas Pag comprise different repeating units of formula -A-O— that are arranged statistically.

It has furthermore proven to be advantageous if the alcohol that is esterified with polyisobutene succinic acid is constructed, at a proportion of at least 50 mole percent (mol %), and in particular at least 70 mol %, based on the total number of alkylene oxide repeating units in the alcohol, from repeating units of the formula [$CH_2CH_2O$]. Correspondingly, in formulas III and Pag the proportion of repeating units of formula [$CH_2CH_2O$] is at least 50 mol % and in particular at least 70 mol %, based on the total number of repeating units A-O.

In a special embodiment of the invention, all or almost all the repeating units A-O of the poly-$C_2$ to $C_4$ alkylene glycol or of the poly-$C_2$ to $C_4$ alkylene glycol mono-$C_1$ to $C_{20}$ alkyl ether, or all or almost all the repeating units A-O in formulas III and Pag, are repeating units of the formula [$CH_2CH_2O$].

In a further preferred embodiment of the invention, the alcohol that is esterified with polyisobutene succinic acid, in particular the alcohol of formula III or the residue Pag, encompasses
  50 mol % to 99 mol %, and in particular 70 mol % to 98 mol %, based on the total number of alkylene oxide repeating units in the alcohol, repeating units of the formula [$CH_2CH_2O$], and
  1 mol % to 50 mol %, and in particular 2 mol % to 30 mol %, based on the total number of alkylene oxide repeating units in the alcohol, repeating units of the formula [A'-

O], in which A' denotes $C_3$ to $C_4$ alkanediyl, and in particular repeating units of the formula [$CH_2CH(CH_3)O$].

In a special configuration of this preferred embodiment, the repeating units [$CH_2CH_2O$] and [A'-O] differing from one another are arranged not block-wise but rather in statistically distributed or alternating fashion.

It has further proven to be advantageous if the alcohol constituent and the polyisobutene succinic acid on which the ester is based are selected in such a way that the ester exhibits, on average, a weight ratio of polyisobutene residue to alcohol residue in the range from 10:1 to 1:30, by preference in the range from 1.5:1 to 1:20, and in particular in the range from 1:1 to 1:10.

The composition according to the present invention furthermore contains at least one surfactant from the group consisting of alkylpolyglycosides, amphoacetates, amphodiacetates, betaines, fatty alcohol ethercarboxylic acids, fatty acid sarcosinates, cocamidopropylamine oxide, aminopropionates, and biosurfactants.

Alkylpolyglycosides are nonionic surfactants that can be obtained by reacting sugars and alcohols in accordance with relevant methods of preparative organic chemistry, the result being (depending on how they are manufactured) a mixture of monoalkylated, oligomeric, or polymeric sugars. Preferred alkylpolyglycosides are the alkylpolyglucosides; particularly preferably, the alcohol is a long-chain fatty alcohol or a mixture of long-chain fatty alcohols having branched or unbranched $C_8$ to $C_{18}$ alkyl chains, and the degree of oligomerization (DP) of the sugars is between 1 and 10, by preference 1 and 6, in particular 1.1 and 3, extremely preferably 1.1 and 1.7, for example $C_{8-10}$ alkyl-1,5-glucoside (DP=1.5).

Amphoacetates, amphodiacetates, and betaines are among the amphosurfactants. Cocoamphodiacetate and/or cocamidopropyl betaine are preferably used in this context.

The fatty acid sarcosinates are condensation products of fatty acids with sarcosine (N-methylglycine). Like the fatty alcohol ethercarboxylic acids, they are included among the anionic surfactants.

The biosurfactants include, for example, saponines or also glycolipids. Glycolipids in the narrower sense are compounds in which one or more monosaccharide units are glycosidically bound to a lipid component. Preferred glycolipids are sophorolipids, rhamnolipids, glucose lipids, cellobiose lipids, trehalose lipids, and mixtures thereof.

Perfume

The composition according to the present invention contains one or more scents, by preference in a quantity from 0.01 to 15 wt %, in particular 0.05 to 10 wt %, particularly preferably 0.1 to 8 wt %. d-Limonene can be contained as a perfume component. In a particularly preferred embodiment, the composition contains a perfume made of essential oils. Usable as such for purposes of this invention are, for example, pine, citrus, jasmine, patchouli, rose, or ylang-ylang oil. Also suitable are muscatel sage oil, chamomile oil, lavender oil, clove oil, lemon balm oil, mint oil, cinnamon leaf oil, linden blossom oil, juniper berry oil, vetiver oil, olibanum oil, galbanum oil, and labdanum oil, as well as orange blossom oil, neroli oil, orange peel oil, and sandalwood oil.

Adherent fragrances that are advantageously usable in the perfume oils in the context of the present invention are, for example, the essential oils such as angelica oil, anise oil, arnica flower oil, basil oil, bay oil, champaca flower oil, silver fir oil, silver fir cone oil, elemi oil, eucalyptus oil, fennel oil, fir needle oil, galbanum oil, geranium oil, gingergrass oil, guaiac wood oil, balsam gurjun oil, helichrysum oil, ho oil, ginger oil, iris oil, cajeput oil, calamus oil, chamomile oil, camphor oil, kanaga oil, cardamom oil, cassia oil, pine needle oil, balsam copaiva oil, coriander oil, curled peppermint oil, caraway oil, cumin oil, lemon grass oil, ambrette seed oil, myrrh oil, clove oil, neroli oil, niaouli oil, olibanum oil, oregano oil, palmarosa oil, patchouli oil, balsam peru oil, petitgrain oil, pepper oil, peppermint oil, pimento oil, pine oil, rose oil, rosemary oil, sandalwood oil, celery oil, star anise oil, thuja oil, thyme oil, verbena oil, vetiver oil, juniper berry oil, wormwood oil, wintergreen oil, ylang-ylang oil, hyssop oil, cinnamon oil, cinnamon leaf oil, and cypress oil.

The higher-boiling or solid fragrances of natural or synthetic origin can, however, also be used advantageously in the context of the present invention as adherent fragrances or fragrance mixtures. Included among these compounds are the compounds recited below as well as mixtures thereof: ambrettolide, α-amyl cinnamaldehyde, anethole, anisealdehyde, anise alcohol, anisole, anthranilic acid methyl ester, acetophenone, benzyl acetone, benzaldehyde, benzoic acid ethyl ester, benzophenone, benzyl alcohol, borneol, bornyl acetate, α-bromostyrene, n-decylaldehyde, n-dodecylaldehyde, eugenol, eugenol methyl ether, eucalyptol, farnesol, fenchone, fenchyl acetate, geranyl acetate, geranyl formate, heliotropin, heptyne carboxylic acid methyl ester, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarin, p-methoxyacetophenone, methyl n-amyl ketone, methylanthranilic acid methyl ester, p-methylacetophenone, methylchavicol, p-methylquinoline, methyl β-naphthyl ketone, methyl-n-nonylacetaldehyde, methyl n-nonyl ketone, muscone, β-naphthol ethyl ether, β-naphthol methyl ether, nerol, nitrobenzene, n-nonylaldehyde, nonyl alcohol, n-octylaldehyde, p-oxyacetophenone, pentadecanolide, β-phenylethyl alcohol, phenylacetaldehyde dimethyl acetal, phenylacetic acid, pulegone, safrole, salicylic acid isoamyl ester, salicylic acid methyl ester, salicylic acid hexyl ester, salicylic acid cyclohexyl ester, santalol, skatole, terpineol, thymene, thymol, γ-undelactone, vanillin, veratrumaldehyde, cinnamaldehyde, cinnamyl alcohol, cinnamic acid, cinnamic acid ethyl ester, cinnamic acid benzyl ester.

Included among the more-volatile fragrances that are advantageously usable in the perfume oils in the context of the present invention are, in particular, the lower-boiling fragrances of natural or synthetic origin, which can be used alone or in mixtures. Examples of more-volatile fragrances are alkyl isothiocyanates (alkyl mustard oils), butanedione, limonene, linalool, linalyl acetate and propionate, menthol, menthone, methyl-n-heptenone, phellandrene, phenylacetaldehyde, terpinyl acetate, citral, citronellal.

Further Ingredients

Besides the components already recited, the composition according to the present invention can contain further usual ingredients of toilet cleaning agents, selected by preference from the group encompassing acids, bases, salts, thickening agents, antimicrobial active substances, preservatives, complexing agents, polymers, dyes, perfume boosters, fillers, builders, bleaching agents, bittering agents, corrosion inhibitors, enzymes, microorganisms, active substances for biofilm removal, active substances to inhibit lime deposition, active substances to decrease dirt adhesion, and mixtures thereof. In total no more than 60 wt % of other ingredients should be contained, by preference 0.01 to 40 wt %, in particular 0.2 to 35 wt %.

Acids

Compositions according to the present invention can contain one or more acids and/or salts thereof in order to intensify cleaning performance with respect to lime and urine scale. The acids are preferably manufactured from renewable raw materials. Suitable acids are therefore, in particular, organic acids such as acetic acid, citric acid, glycolic acid, lactic acid, succinic acid, adipic acid, malic acid, tartaric acid, and gluconic acid, as well as mixtures thereof. Amidosulfonic acid can, however, also be used. The acids and/or salts thereof can be selected particularly preferably from the group encompassing citric acid, lactic acid, amidosulfonic acid, salts thereof and mixtures thereof. They are used by preference in quantities from 0.01 to 10 wt %, particularly preferably 0.2 to 5 wt %.

In an embodiment, the composition can in addition contain inorganic salts, by preference alkali or alkaline-earth metal salts, in particular carbonates, sulfates, halides, or phosphates, as well as mixtures thereof. Particularly preferably, sodium sulfate and/or sodium carbonate are used. Sodium sulfate can be contained in a quantity of up to 60 wt %, by preference 0.01 to 60 wt %, particularly preferably 20 to 60 wt %, in particular 35 to 55 wt %. Sodium carbonate and further salts can be contained in a quantity of up to 30 wt %, by preference up to 10 wt %, particularly preferably up to 5 wt %.

Bases

Alkalis can furthermore be contained in compositions according to the present invention. The bases used in agents according to the present invention are by preference those from the group of the alkali and alkaline-earth metal hydroxides and carbonates, in particular sodium carbonate or sodium hydroxide. Ammonia and/or alkanolamines having up to 9 carbon atoms in the molecule can, however also be used besides, by preference the ethanolamines, in particular monoethanolamine.

Antimicrobial Active Substances

Disinfection and sanitization represent a particular form of cleaning. In a corresponding particular embodiment of the invention, the gel or paste therefore contains one or more antimicrobial active substances, in a quantity by preference of up to 40 wt %, preferably 0.01 to 25 wt %, in particular 0.1 to 5 wt %.

The terms "disinfection," "sanitization," "antimicrobial action," and "antimicrobial active substance" have, in the context of the teaching of the present invention, the meaning usual in the art. While "disinfection" in the narrow context of medical practice means the destruction of (theoretically, all) infectious germs, "sanitization" is to be understood as the most complete possible elimination of all germs, including the saprophytic ones normally harmless to humans. The degree of disinfection or sanitization depends on the antimicrobial action of the agent that is utilized, which decreases with decreasing concentration of the antimicrobial active substance or increasing dilution of the agent being used.

Antimicrobial active substances suitable according to the present invention are, for example, those from the groups of the alcohols, aldehydes, antimicrobial acids or salts thereof, carboxylic acid esters, acid amides, phenols, phenol derivatives, diphenyls, diphenylalkanes, urea derivatives, oxygen and nitrogen acetals and oxygen and nitrogen formals, benzamidines, isothiazoles and derivatives thereof such as isothiazolines and isothiazolinones, phthalimide derivatives, pyridine derivatives, antimicrobial surface-active compounds, guanidines, antimicrobial amphoteric compounds, quinolines, 1,2-dibromo-1,4-dicyanobutane, iodo-2-propynyl butylcarbamate, iodine, iodophores, compounds that release active chlorine, and peroxides. Preferred antimicrobial active substances are selected by preference from the group encompassing 1,3-butanediol, phenoxyethanol, 1,2-propylene glycol, glycerol, undecylenic acid, citric acid, lactic acid, benzoic acid, salicylic acid, thymol, 2-benzyl-4-chlorophenol, 2,2'-methylene-bis-(6-bromo-4-chlorophenol), 2,4,4'-trichloro-2'-hydroxydiphenyl ether, N-(4-chlorophenyl)-N-(3,4-dichlorophenyl)urea, N,N'-(1,10-decanediyldi-1-pyridinyl-4-ylidene)-bis-(1-octanamine) dihydrochloride, N,N'-bis-(4-chlorophenyl)-3,12-diimino-2,4,11,13-tetraazatetradecanediimideamide, antimicrobial quaternary surface-active compounds, guanidines, trichloroisocyanuric acid and sodium dichloroisocyanurate (DCI, 1,3-dichloro-5H-1,3,5-triazine-2,4,6-trione sodium salt). Preferred surface-active quaternary compounds having antimicrobial activity contain an ammonium, sulfonium, phosphonium, iodonium, or arsonium group. Antimicrobially effective essential oils, which at the same time provide scenting of the cleaning agent, can also be used. Particularly preferred antimicrobial active substances are selected, however, from the group encompassing salicylic acid, quaternary surfactants, in particular benzalkonium chloride, peroxo compounds, in particular sodium percarbonate or phthalimidoperoxyhexanoic acid, alkali metal hypochlorite, trichloroisocyanuric acid, sodium dichloroisocyanurate, and mixtures thereof.

Preservatives

Preservatives can likewise be contained in compositions according to the present invention. The substances that can be used for this purpose are substantially those recited in the context of the antimicrobial active substances.

Complexing Agents

Complexing agents (INCI: Chelating Agents), also called "sequestering agents," are ingredients that are capable of complexing and inactivating metal ions in order to prevent their disadvantageous effects on the stability or appearance of the agents, for example clouding. On the one hand it is important to complex the calcium and magnesium ions of water hardness, which are incompatible with numerous ingredients. Complexing of ions of heavy metals such as iron or copper, on the other hand, delays oxidative breakdown of the complete agents. Complexing agents moreover assist the cleaning effect.

For example, the following complexing agents, designated according to INCI, are suitable. Aminotrimethylene Phosphonic Acid, Beta-Alanine Diacetic Acid, Calcium Disodium EDTA, Citric Acid, Cyclodextrin, Cyclohexanediamine Tetraacetic Acid, Diammonium Citrate, Diammonium EDTA, Diethylenetriamine Pentamethylene Phosphonic Acid, Dipotassium EDTA, Disodium Azacycloheptane Diphosphonate, Disodium EDTA, Disodium Pyrophosphate, EDTA, Etidronic Acid, Galactaric Acid, Gluconic Acid, Glucuronic Acid, HEDTA, Hydroxypropyl Cyclodextrin, Methyl Cyclodextrin, Pentapotassium Triphosphate, Pentasodium Aminotrimethylene Phosphonate, Pentasodium Ethylenediamine Tetramethylene Phosphonate, Pentasodium Pentetate, Pentasodium Triphosphate, Pentetic Acid, Phytic Acid, Potassium Citrate, Potassium EDTMP, Potassium Gluconate, Potassium Polyphosphate, Potassium Trisphosphonomethylamine Oxide, Ribonic Acid, Sodium Chitosan Methylene Phosphonate, Sodium Citrate, Sodium Diethylenetriamine Pentamethylene Phosphonate, Sodium Dihydroxyethylglycinate, Sodium EDTMP, Sodium Gluceptate, Sodium Gluconate, Sodium Glycereth-1 Polyphosphate, Sodium Hexametaphosphate, Sodium Metaphosphate, Sodium Metasilicate, Sodium Phytate, Sodium Polydimethylglycinophenolsulfonate, Sodium Trimetaphosphate, TEA-EDTA, TEA-Polyphosphate, Tetrahydroxyethyl Ethylenediamine, Tetrahydroxypropyl Ethylenediamine, Tetrapotassium Etidronate, Tetrapotassium Pyrophosphate, Tetrasodium EDTA, Tetrasodium Etidronate, Tetrasodium Pyrophosphate, Tripotassium EDTA, Trisodium Dicarboxymethyl Alaninate, Trisodium EDTA, Trisodium HEDTA, Trisodium NTA, and Trisodium Phosphate.

Polymers

The toilet cleaning block according to the present invention can furthermore contain polymers. These can serve, for example, to reduce both lime formation and susceptibility to re-soiling. Preferred polymers are acrylic copolymers such as, for example, those commercially obtainable from the Rhodia company under the trade name Mirapol.

Dyes

As further ingredients, the composition according to the present invention can contain one or more dyes (INCI: Colorants). Both water-soluble and oil-soluble dyes can be used as dyes; on the one hand attention must be paid to compatibility with further ingredients, for example bleaching agents, and on the other hand the dye used should not have a substantive effect on the toilet ceramic even after extended contact. The dyes are contained by preference in a quantity from 0.0001 to 5 wt %, in particular 0.0005 to 0.25 wt %, particularly preferably 0.0008 to 0.08 wt %.

Builders

Water-soluble and/or water-insoluble builders can optionally be used in the compositions according to the present invention. Water-soluble builders are preferred, since as a rule they have less tendency to leave insoluble residues on hard surfaces. Usual builders that can be added in the context of the invention are the low-molecular-weight polycarboxylic acids and salts thereof, the homopolymeric and copolymeric polycarboxylic acids and salts thereof, citric acid and salts thereof, carbonates, phosphates, and silicates. Water-insoluble builders include the zeolites, which can likewise be used, as well as mixtures of the aforesaid builder substances.

Bleaching Agents

According to the present invention, bleaching agents can be added to the cleaning agent. Suitable bleaching agents encompass peroxides, peracids, and/or perborates; sodium percarbonate or phthalimidoperoxyhexanoic acid is particularly preferred. Chlorine-containing bleaching agents such as trichloroisocyanuric acid or sodium dichloroisocyanurate, on the other hand, are less suitable for acid-formulated cleaning agents due to the release of toxic chlorine gas vapors, but can be used in cleaning agents adjusted to be alkaline. In some circumstances a bleach activator can also be necessary alongside the bleaching agent.

Corrosion Inhibitors

Suitable corrosion inhibitors (INCI Corrosion Inhibitors) are, for example, the following substances recited in accordance with INCI: Cyclohexylamine, Diammonium Phosphate, Dilithium Oxalate, Dimethylamino Methylpropanol, Dipotassium Oxalate, Dipotassium Phosphate, Disodium Phosphate, Disodium Pyrophosphate, Disodium Tetrapropenyl Succinate, Hexoxyethyl Diethylammonium, Phosphate, Nitromethane, Potassium Silicate, Sodium Aluminate, Sodium Hexametaphosphate, Sodium Metasilicate, Sodium Molybdate, Sodium Nitrite, Sodium Oxalate, Sodium Silicate, Stearamidopropyl Dimethicone, Tetrapotassium Pyrophosphate, Tetrasodium Pyrophosphate, Triisopropanolamine.

Enzymes

The composition can also contain enzymes, by preference proteases, lipases, amylases, hydrolases, and/or cellulases. They can be added to the agent according to the present invention in any form established in the existing art. This includes solutions of the enzymes, advantageously maximally concentrated, low in water, and/or with stabilizers added. Alternatively, the enzymes can be encapsulated, for example by spray drying or extrusion of the enzyme solution together with a (preferably natural) polymer or in the form of capsules, for example those in which the enzymes are enclosed as if in a solidified gel or in those of the core-shell type, in which an enzyme-containing core is coated with a protective layer that is impermeable to water, air, and/or chemicals. Further active substances, for example stabilizers, emulsifier agents, pigments, bleaches, or dyes can additionally be applied in superimposed layers. Such capsules are applied using methods known per se, for example by vibratory or roll granulation or in fluidized bed processes. Advantageously, such granulates are low in dust, for example thanks to the application of polymeric film formers, and are shelf-stable as a result of the coating. Enzyme stabilizers can furthermore be present in enzyme-containing agents in order to protect an enzyme contained in an agent according to the present invention from damage such as, for example, inactivation or denaturing, for example as a result of physical influences, oxidation, or proteolytic cleavage.

The following are particularly suitable as enzyme stabilizers, depending in each case on the enzyme being used: benzamidine hydrochloride, borax, boric acids, boronic acids, or salts or esters thereof, principally derivatives having aromatic groups, e.g. substituted phenylboronic acids or salts or esters thereof; peptide aldehydes (oligopeptides having a reduced carbon terminus), aminoalcohols such as mono-, di-, triethanol- and -propanolamine and mixtures thereof, aliphatic carboxylic acids up to $C_{12}$ such as succinic acid, other dicarboxylic acids or salts of the aforesaid acids; end-capped fatty acid amide alkoxylates; lower aliphatic alcohols and especially polyols, for example glycerol, ethylene glycol, propylene glycol, or sorbitol; as well as reducing agents and antioxidants such as sodium sulfite and reducing sugars. Further suitable stabilizers are known from the existing art. It is preferred to use combinations of stabilizers, for example the combination of polyols, boric acid, and/or borax, the combination of boric acid or borate, reducing salts, and succinic acid or other dicarboxylic acids, or the combination of boric acid or borate with polyols or polyamino compounds and with reducing salts.

The composition is advantageously applied with an applicator. It may be desirable for aesthetic reasons, but also so that mutually incompatible active substances can be utilized together, to simultaneously apply two or even more portions of the adherent gel or paste according to the present invention next to one another onto the toilet ceramic. A two-chamber applicator, as also described in patent application DE 10 2010 028352.5, is particularly suitable for this. This applicator can stock gels or pastes of identical or different composition in its two chambers.

Upon use, usually a quantity from 4 to 8 g of the composition is applied onto the toilet ceramic using the applicator. This application quantity is advantageously completely dissolved off after 100 to 200 flushing operations.

The agent according to the present invention is manufactured by mixing the individual components and then decanting them. Suitable as a mixer are all machines that can process viscous substances, for example a SpeedMixer, planetary mixer, or static mixer. To minimize losses of volatile ingredients, in particular in the case of perfume, processing occurs at the lowest possible temperature, but at a maximum of 85° C. The polymer is melted at this temperature, and surfactants, perfume oil, and further components are added while stirring in the mixer. In the warm state the formulation is flowable and can be decanted.

EXEMPLIFYING EMBODIMENTS

Two gel-type formulations E1 and E2 were manufactured, and were decanted as a multi-phase agent into a two-chamber applicator. E1 here served principally for scenting, while E2 represents a cleaning formula. The compositions are evident from the table below. The indications of quantity are in wt % active substance.

TABLE 1

|  | E1 | E2 |
|---|---|---|
| Esters of polyisobutene succinic acid | 46.00 | 46.00 |
| Alkylpolyglucoside | 9.10 | 9.10 |
| Cocamidopropyl betaine | 6.29 | 6.29 |
| Perfume oil | 4.90 | 4.90 |
| Bittering agent (Bitrex) | 0.0010 | 0.0010 |
| Trisodium citrate | — | 0.10 |
| Dye, yellow | 0.0150 | — |
| Dye, blue | — | 0.0130 |
| Water (demineralized) | to 100 | to 100 |

While at least one exemplary embodiment has been presented in the foregoing detailed description of the invention, it should be appreciated that a vast number of variations exist. It should also be appreciated that the exemplary embodiment or exemplary embodiments are only examples, and are not intended to limit the scope, applicability, or configuration of the invention in any way. Rather, the foregoing detailed description will provide those skilled in the art with a convenient road map for implementing an exemplary embodiment of the invention, it being understood that various changes may be made in the function and arrangement of elements described in an exemplary embodiment without departing from the scope of the invention as set forth in the appended claims and their legal equivalents.

What is claimed is:

1. An adherent gelled or pasty composition for cleaning and/or scenting a toilet, wherein the composition is applied internally onto the toilet ceramic and is rinsed off only after several flushing operations, the composition comprising:
   a surfactant selected from the group consisting of alkylpolyglycosides, amphoacetates, amphodiacetates, betaines, fatty alcohol ethercarboxylic acids, fatty acid sarcosinates, cocamidopropylamine oxide, aminopropionates, and biosurfactants;
   perfume; and
   water;
      wherein the composition comprises, as an adhesion promoter, an ester of polyisobutene succinic acid, and wherein the composition is free of further adhesion promoters and surfactants.

2. The adherent composition of claim 1, wherein the ester of polyisobutene succinic acid is present in an amount of 20 to 80 wt %.

3. The adherent composition of claim 2, wherein the ester of polyisobutene succinic acid is present in an amount of 30 to 70 wt %.

4. The adherent composition of claim 1, wherein the composition comprises alkylpolyglycoside in an amount of 0 to 40 wt %.

5. The adherent composition of claim 4, wherein the alkylpolyglycoside is present in an amount of 2 to 35 wt %.

6. The adherent composition of claim 1, wherein the surfactant is selected from the group consisting of amphoacetates, amphodiacetates, betaines, fatty alcohol ethercarboxylic acids, fatty acid sarcosinates, cocamidopropylamine oxide, aminopropionates, and biosurfactants in an amount of 0 to 40 wt %.

7. The adherent composition of claim 6, wherein the surfactant is present in an amount of 2 to 35 wt %.

8. The adherent composition of claim 1, comprising alkylpolyglycoside and a surfactant selected from the group consisting of amphoacetates, amphodiacetates, betaines, fatty alcohol ethercarboxylic acids, fatty acid sarcosinates, cocamidopropylamine oxide, aminopropionates, and biosurfactants.

9. The adherent composition of claim 1, further comprising toilet cleaning agents selected from the group consisting of acids, bases, salts, thickening agents, antimicrobial active substances, preservatives, complexing agents, dyes, perfume boosters, fillers, builders, bleaching agents, bittering substances, corrosion inhibitors, enzymes, microorganisms, active substances for biofilm removal, active substances to inhibit lime deposition, active substances to decrease dirt adhesion, and mixtures thereof.

10. The adherent composition of claim 1, wherein an application quantity of 4 to 8 g is completely dissolved off after 100 to 200 flushing operations.

11. The adherent composition of claim 1, wherein the composition is applied by an applicator onto the toilet ceramic and adheres thereto.

12. The adherent composition of claim 11, wherein two portions of the composition are simultaneously applied next to one another with the applicator.

13. The adherent composition of claim 12, wherein the applicator comprises two chambers wherein gels or pastes of identical or different composition are stocked.

* * * * *